(12) United States Patent
Papac et al.

(10) Patent No.: US 8,688,401 B2
(45) Date of Patent: Apr. 1, 2014

(54) PROVIDING CONSISTENT OUTPUT FROM AN ENDOILLUMINATOR SYSTEM

(75) Inventors: Michael J. Papac, North Tustin, CA (US); John C. Huculak, Mission Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 346 days.

(21) Appl. No.: 13/334,333

(22) Filed: Dec. 22, 2011

(65) Prior Publication Data

US 2013/0163276 A1 Jun. 27, 2013

(51) Int. Cl.
*G06F 15/00* (2006.01)

(52) U.S. Cl.
USPC .......................... 702/127; 362/574; 351/221

(58) Field of Classification Search
USPC .................. 362/572, 574; 702/127; 351/221
See application file for complete search history.

(56) References Cited

U.S. PATENT DOCUMENTS

| | | | |
|---|---|---|---|
| 3,327,712 A | 6/1967 | Kaufman et al. |
| 3,703,176 A | 11/1972 | Vassiliadis et al. |
| 3,930,504 A | 1/1976 | de Laforcade |
| 4,068,956 A | 1/1978 | Taboada |
| 4,165,180 A | 8/1979 | Failes |
| 4,270,845 A | 6/1981 | Takizawa et al. |
| 4,275,288 A | 6/1981 | Makosch et al. |
| 4,418,689 A | 12/1983 | Kanazawa |
| 4,542,956 A | 9/1985 | McCrickerd |
| 4,626,999 A | 12/1986 | Bannister |
| 4,729,621 A | 3/1988 | Edelman |
| 5,300,062 A | 4/1994 | Ueno |
| 5,336,216 A | 8/1994 | Dewey |
| 5,357,312 A | 10/1994 | Tounai |
| 5,405,659 A | 4/1995 | Fernandez |
| 5,550,367 A | 8/1996 | Plesko |
| 5,734,934 A | 3/1998 | Horinishi et al. |
| 5,754,719 A | 5/1998 | Chen et al. |
| 5,856,721 A | 1/1999 | Gordin et al. |
| 5,933,274 A | 8/1999 | DeSimone |
| 5,947,957 A | 9/1999 | Morris |
| 6,154,595 A | 11/2000 | Yokogawa et al. |
| 6,254,264 B1 | 7/2001 | Koshikawa et al. |
| 6,587,276 B2 | 7/2003 | Daniell |
| 6,614,512 B1 | 9/2003 | Sakamoto et al. |
| 6,628,877 B2 | 9/2003 | Dugan et al. |
| 6,690,702 B1 | 2/2004 | Ohmi et al. |
| 6,721,101 B2 | 4/2004 | Daniell |
| 6,928,239 B2 | 8/2005 | Fukui |

(Continued)

FOREIGN PATENT DOCUMENTS

| | | |
|---|---|---|
| EP | 0687956 B2 | 11/2005 |
| JP | 2001017380 A | 1/2001 |

(Continued)

*Primary Examiner* — Stephen F Husar
*Assistant Examiner* — James Cranson, Jr.

(57) ABSTRACT

In certain embodiments, determining an endoilluminator output includes calculating an illuminator contribution of an endoilluminator system and a fiber contribution of one or more optical fibers of the endoilluminator system. The endoilluminator output is determined from the illuminator contribution and the fiber contribution. The illuminator contribution may be established using calibrated or empirically determined factors, such as an illuminator leg efficiency, an attenuator factor, an initial lamp performance, and/or a lamp performance degradation factor of the lamp. The fiber contribution may be established using calibrated or empirically determined factors, such as a fiber coupling factor and/or fiber transmission ratio of the optical fibers.

26 Claims, 4 Drawing Sheets

(56) References Cited

U.S. PATENT DOCUMENTS

| | | |
|---|---|---|
| 7,102,700 B1 | 9/2006 | Pease et al. |
| 7,142,257 B2 | 11/2006 | Callison et al. |
| 7,174,067 B2 | 2/2007 | Murshid et al. |
| 7,292,323 B2 | 11/2007 | Artsyukhovich et al. |
| 7,418,172 B2 | 8/2008 | Tanaka et al. |
| 7,474,339 B2 | 1/2009 | Hoshuyama |
| 7,502,178 B2 | 3/2009 | Shenderova et al. |
| 7,599,591 B2 | 10/2009 | Andersen et al. |
| 7,611,256 B2 | 11/2009 | Becker et al. |
| 7,639,909 B2 | 12/2009 | Murshid et al. |
| 7,682,027 B2 | 3/2010 | Buczek et al. |
| 8,126,302 B2 | 2/2012 | Rowe et al. |
| 8,474,977 B2 * | 7/2013 | Hahn et al. .................... 351/221 |
| 8,480,279 B2 * | 7/2013 | Papac et al. .................... 362/572 |
| 8,485,972 B2 * | 7/2013 | Papac et al. .................... 600/249 |
| 2002/0140379 A1 | 10/2002 | Chevalier et al. |
| 2002/0180869 A1 | 12/2002 | Callison et al. |
| 2003/0112523 A1 | 6/2003 | Daniell |
| 2004/0213514 A1 | 10/2004 | Tanaka et al. |
| 2005/0046944 A1 | 3/2005 | Shenderova et al. |
| 2005/0117209 A1 | 6/2005 | Moller et al. |
| 2006/0033926 A1 | 2/2006 | Artsyukhovich et al. |
| 2006/0103835 A1 | 5/2006 | Artsyukhovich et al. |
| 2006/0268231 A1 | 11/2006 | Gil et al. |
| 2006/0274321 A1 | 12/2006 | Cottrell |
| 2007/0024836 A1 | 2/2007 | Singer et al. |
| 2007/0085936 A1 | 4/2007 | Callison et al. |
| 2007/0139924 A1 | 6/2007 | Easley et al. |
| 2007/0189664 A1 | 8/2007 | Andersen et al. |
| 2008/0224966 A1 | 9/2008 | Cok et al. |
| 2008/0230723 A1 | 9/2008 | Tanaka et al. |

FOREIGN PATENT DOCUMENTS

| | | |
|---|---|---|
| WO | 9009607 A1 | 8/1990 |
| WO | 2005016118 A2 | 2/2005 |
| WO | 2006053273 A2 | 5/2006 |
| WO | 2007115034 A2 | 10/2007 |

* cited by examiner

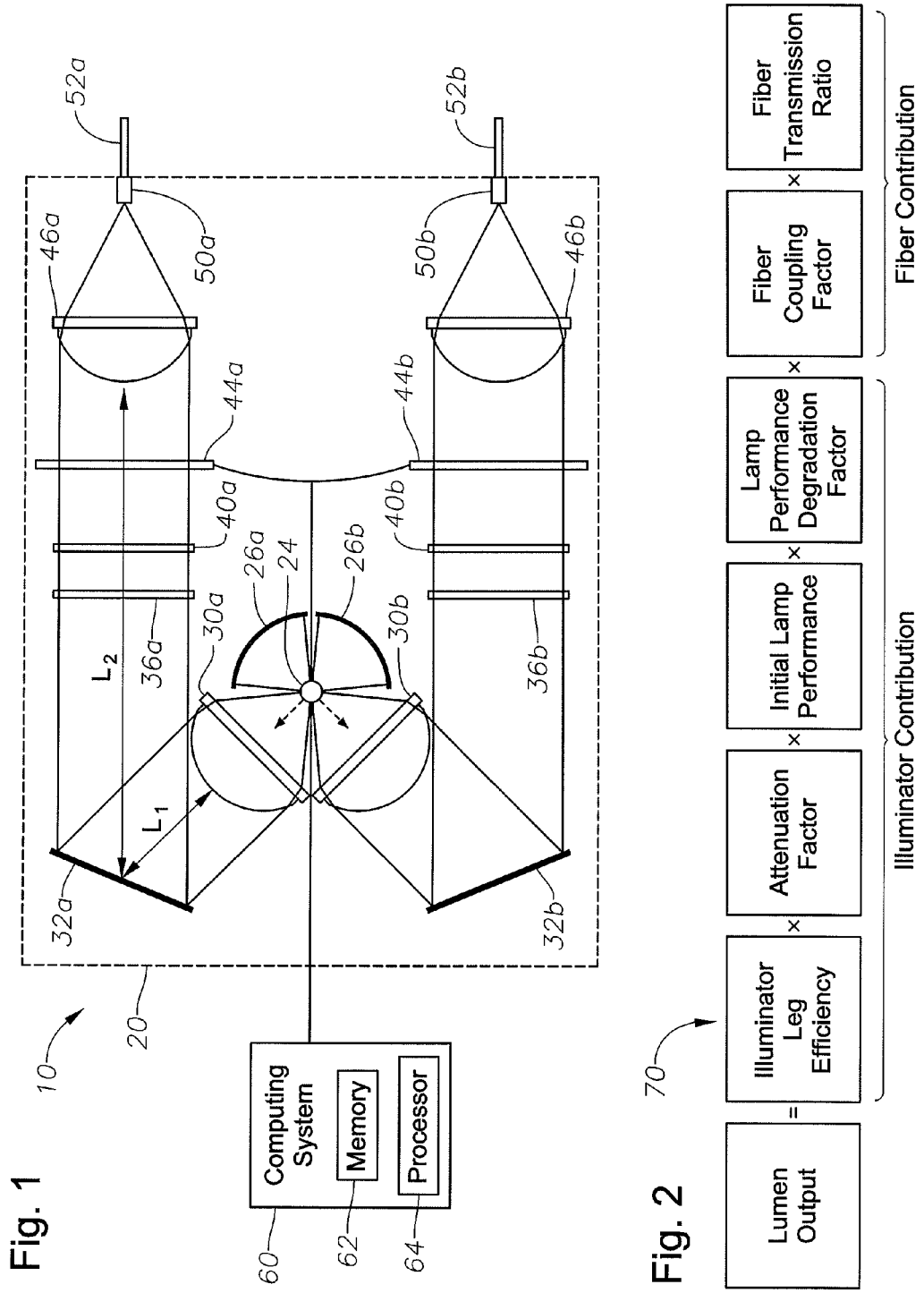

PROVIDING CONSISTENT OUTPUT FROM AN ENDOILLUMINATOR SYSTEM

TECHNICAL FIELD

The present disclosure relates generally to endoilluminators, and more particularly to providing consistent output from an endoilluminator system.

BACKGROUND

An endoilluminator system has an endoilluminator probe that projects light to illuminate a target, such as an interior region of a part of a human (e.g., an eyeball) or other organism. For example, an endoillumination system may include an illumination console in addition to the endoilluminator probe. The illumination console houses a light source and optics that focus light from the source onto a connector port. The endoilluminator probe has a proximal end that connects to the illumination console at the port and a distal end that projects illuminating light. The output of the endoilluminator system describes the output at the distal end of the endoilluminator probe. Information regarding the endoilluminator output can be important to the user. For example, in vitreoretinal surgery, the amount of light is controlled to avoid excessive exposure to the retina. Certain known endoilluminator systems, however, fail to provide a technique for calculating the endoilluminator output that is accurate and efficient in certain situations.

BRIEF SUMMARY

In certain embodiments, determining an endoilluminator output includes calculating an illuminator contribution of an endoilluminator system and a fiber contribution of one or more optical fibers of the endoilluminator system. The endoilluminator output is determined from the illuminator contribution and the fiber contribution. The illuminator contribution may be established using calibrated or empirically determined factors, such as an illuminator leg efficiency, an attenuator factor, an initial lamp performance, and/or a lamp performance degradation factor of the lamp. The fiber contribution may be established using calibrated or empirically determined factors, such as a fiber coupling factor and/or fiber transmission ratio of the optical fibers.

BRIEF DESCRIPTION OF THE DRAWINGS

Exemplary embodiments of the present disclosure will now be described by way of example in greater detail with reference to the attached figures, in which:

FIG. 1 illustrates an example of a system for which output may be calculated according to certain embodiments;

FIG. 2 illustrates an example of a method for calculating an endoilluminator output according to certain embodiments;

DETAILED DESCRIPTION OF THE INVENTION

Figure 3:
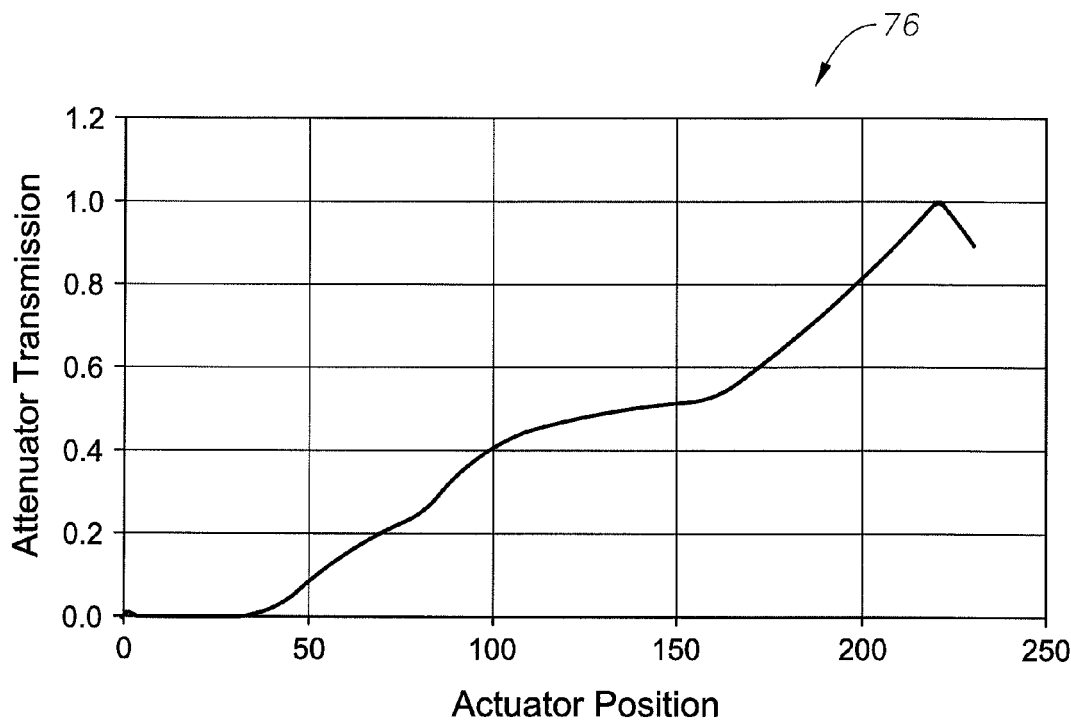
FIG. 3 illustrates an example of an attenuator factor according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of a system 10 for which an endoilluminator output may be calculated. System 10 may be located in an optical envelope 20 of a console of an endoilluminator system. The endoilluminator system may have an endoilluminator probe that projects light to illuminate a target, such as a region of a human or other organism. For example, an endoilluminator probe may be a surgical instrument that projects illuminating light into an interior of an eyeball.

In the illustrated example, system 10 includes a lamp (or illuminator) 24, spherical mirrors 26 (26a-b), lenses 30 (30a-b), cold mirrors 32 (32a-b), hot mirrors 36 (36a-b), filters 40 (40a-b), attenuators 44 (44a-b), lenses 46 (46a-b), ports (50a-b), optical fibers (52a-b), and computing system 60 (which includes one or more memories 62 and one or more processors 64) optically, electrically, and/or mechanically coupled as illustrated. In an example of operation, lamp 24 provides light, which is directed towards lenses 30 and/or reflected by spherical mirrors 26 towards lenses 30. Lenses 30 collimate and direct light towards cold mirrors 32, which transmit infrared light and reflect visible light towards hot mirrors 36. Hot mirrors 36 pass through the visible light towards filters 40, which filter for the remaining ultraviolet and infrared light. Attenuators 44 attenuate the light directed towards lenses 46, which focus the light towards ports 50. Ports couple the light to optical fibers 52.

In particular embodiments, lamp 24 may be any suitable light source, for example, an arc-lamp, light emitting diode (LED), or laser light source. Different types of lamps 24 may be used with system 10. For example, a particular type of lamp may be used and then replaced with another type of lamp. A mirror 26 may be any suitable optical device (such as a reflective surface) that directs (such as reflects) light towards lens 30. For example, mirror 26 may be a spherical mirror. A lens 30 may be any suitable optical device that collimates light. For example, lens 30 may be an aspheric condensing lens.

A cold mirror 32 may be any suitable optical device (such as a reflective surface) that directs (such as reflects) light towards hot mirror 36. For example, cold mirror 32 may be a dielectric mirror, or a dichroic filter, that reflects visible light while transmitting infrared light. A hot mirror 36 may be any suitable optical device (such as an optical filter) that directs (such as transmits) light towards hot mirror filter 40. For example, hot mirror 36 may be a dielectric mirror, or a dichroic filter, that transmits visible light while reflecting infrared light.

An auxiliary filter may be used to change the color of the illumination light. An attenuator 44 (44a-b) may be any suitable device that attenuates light, such as a louver attenuator. A lens 46 may be any suitable optical device that directs light towards ports 50, such as an aspheric condensing lens that converts collimated light to directed light. A port 50 couples light to an optical fiber 52. An optical fiber 52 may be an optical waveguide that transmits light. Optical fiber 52 may have any suitable diameter, for example, a diameter in the range of 0.1 millimeters (mm) to 1 mm. In certain embodiments, optical fiber 52 delivers the light to a probe, such as an endoilluminator probe.

In certain embodiments, computing system 60 located in the console of an endoilluminator system may be used to control system 10. For example, a user may enter a set point for the output of an endoilluminator system into computing system 60 using, e.g., a graphical user interface (GUI) such as a touch screen. Computing system 60 may control components of system 10 in order to maintain the set point. For example, computing system 60 may calculate the endoilluminator output, determine the difference between the output and the set point, and then adjust the components to compensate for the difference. In certain embodiments, computing system 60 may adjust attenuator 44 and/or light source power to output more or less light. In certain embodiments, computing system 60 may output (e.g., display) the endoilluminator output to the user.

In certain embodiments, computing system 60 may calculate the endoilluminator output using any suitable information, such as calibration and/or empirically determined (such as measured and/or recorded) information. The information may include, e.g., lamp or probe information, such as UFR and FTF information (described below). The information may be collected in any suitable manner, such as using wireless or wired communication, a stored lookup table, user input, a monitoring device that monitors one or more components of system 10, and/or other suitable process or device. For example, a read/write function can track lamp hours.

FIG. 2 illustrates a diagram 70 showing an example of a method for calculating an endoilluminator output. The endoilluminator output describes the output at a port 50 of an endoilluminator system. The output may be the luminous flux output. In certain embodiments, the endoilluminator output may be calculated from a mathematical function of the illuminator contribution of lamp 24 of the endoilluminator system and the fiber contribution of one or more optical fibers 52 of the endoilluminator system.

In certain embodiments, the endoilluminator output may be the product of the illuminator contribution and the fiber contribution. For example the endoilluminator output $\phi_L$ may be described using Equation (1):

$$\phi_L = \text{illuminator contribution} * \text{fiber contribution} \quad (1)$$

The illuminator contribution describes the luminous flux output of the illuminator. In certain embodiments, the illuminator contribution may be a mathematical function of one or more constants that describe lamp 24 and/or one or more time-dependent factors that take into account the age of lamp 24. For example, the constant values may include an illuminator leg efficiency, attenuation factor, and/or initial lamp performance. The time-dependent factors may include a lamp performance degradation factor. In certain embodiments, the illuminator contribution may be directly sampled and measured.

The fiber contribution describes how well optical fibers 52 transmit light. In certain embodiments, the fiber contribution may be a function of constant values and/or time-dependent factors. For example, a constant value may be a fiber coupling factor, and a time-dependent factor may be a fiber transmission ratio.

In certain embodiments, the illuminator contribution and the fiber contribution may be described using Equation (2):

$$\phi_L = \eta_L \times f_L \times I(P_0) \times LIDF(t) \times UFR \times FTF(t) \quad (2)$$

The illuminator contribution is given by $\eta_L f_L \times I(P_0) \times LIDF(t)$, where $\eta_L$ is the illuminator leg efficiency, $f_L$ is the attenuator factor, $I(P_0)$ is the initial lamp performance, and $LIDF(t)$ is the lamp performance degradation factor. The fiber contribution is given by $UFR \times FTF(t)$, where UFR is the fiber transmission ratio of a fiber probe relative to a glass fiber standard (typically measured with a low intensity, stable, diffuse test source) and $FTF(t)$ is the fiber transfer function (which is the coupling ratio of the actual source relative to the test source).

The illuminator leg efficiency measures the percentage of optical efficiency of lamp 24 with respect to a reference lamp, which may be regarded as having the best efficiency. In certain embodiments, the illuminator leg efficiency may be determined during calibration performed during manufacture of lamp 24.

The attenuator factor describes the transmission through an attenuator 44 with respect to position of attenuator 44. In certain embodiments, the attenuator factor may be determined during manufacture of lamp 24. An example of an attenuator factor is described with reference to FIG. 3.

The initial lamp performance describes the initial luminous flux output of lamp 24 through a standard fiber (such as a glass fiber standard that typically does not degrade over the duration of a test). In certain embodiments, the initial lamp performance may be estimated using the power consumption of lamp 24 (measured, e.g., subsequent to the initial warm-up cycle of lamp 24) and a lamp intensity function that describes luminous flux output with respect to power consumption. The lamp intensity function may be determined in any suitable manner, e.g., from empirical data. An example of a lamp intensity function may be described using Equation (3):

$$I(P_0) = \Sigma_{i=0}^{n} C_i P_0^i \quad (3)$$

where $C_i$ are determined empirically, and $n>0$, such as $n>3$, e.g., $n=9$. An example of a lamp intensity function is described with reference to FIG. 4.

The initial lamp performance may be determined in other suitable manners, e.g., by sampling the initial output of lamp 24. In certain embodiments, the initial lamp performance may be adjusted in response to additional data, for example, additional power consumption data. In certain embodiments, a next initial lamp performance may be determined for a next lamp, such as a replacement lamp. The next illuminator contribution of the next lamp may be calculated using the next initial lamp performance, and a next endoilluminator output of the endoilluminator system may be determined from the next illuminator contribution and the fiber contribution.

The lamp performance degradation factor describes the degradation of the intensity of lamp 24 as lamp 24 ages. In certain embodiments, the lamp performance degradation factor may be determined using a lamp intensity degradation function that is a normalized function of lamp age. The lamp performance degradation function may be determined from empirical data. For example, the data may describe how luminous flux measured through a standard fiber degrades as a function of the lamp age. The standard fiber may be, for example, a glass fiber standard (GFS), and may provide an angular and spatial aperture for the light to pass through in a controlled manner. An example of a lamp performance degradation function may be described using Equation (4):

$$LIDF(t) = \Sigma_{i=0}^{n} A_i t^i \quad (4)$$

where $A_i$ are determined empirically, and $n>0$, such as $n>3$, e.g., $n=9$. An example of a lamp intensity degradation function is described with reference to FIG. 5.

The lamp performance degradation may be determined in other suitable manners, e.g., by monitoring lamp power consumption. An example of determining lamp performance using measured power is described with reference to FIG. 6.

The fiber coupling factor describes how the luminous flux degrades as light is directed towards optical fiber 52. The fiber coupling factor may be determined from a fiber transfer function that describes how the luminous flux output of a specific type of probe degrades relative to the luminous flux output through a standard fiber. In certain embodiments, a particular probe type may have a specific fiber transfer function. The fiber transfer function may be determined from empirical data and stored at computing system 60 or the probe. An example of a fiber transfer function may be described using Equation (5):

$$FTF_G(t) = \Sum_{i=0}^n B_i t^i \tag{5}$$

where $B_i$ are determined empirically, and n>0, such as n>3, e.g., n=9. Examples of fiber transfer functions for different types of probes are described in more detail with reference to FIG. 6.

The fiber transmission ratio describes the ratio between the transmission of a particular probe and the transmission of a reference fiber. For example, the fiber transmission ratio may be the universal flux ratio (UFR). In certain embodiments, a code for the fiber transmission ratio may be placed on the probe such that when the probe is connected to system 10, system 10 reads the code to obtain the fiber transmission ratio. The code may be, e.g., a radio frequency identifier (RFID).

FIG. 3 illustrates an example of an attenuator factor. Diagram 76 shows an example of attenuator transmission with respect to attenuator position for a port 50. Attenuator transmission is given in percentage of transmission, and attenuator position is given in units of degrees or stepper motor steps, where a single stepper motion step produces a motion of a predetermined number of degrees per step (e.g., 0.5 degrees/step).

Figure 4:
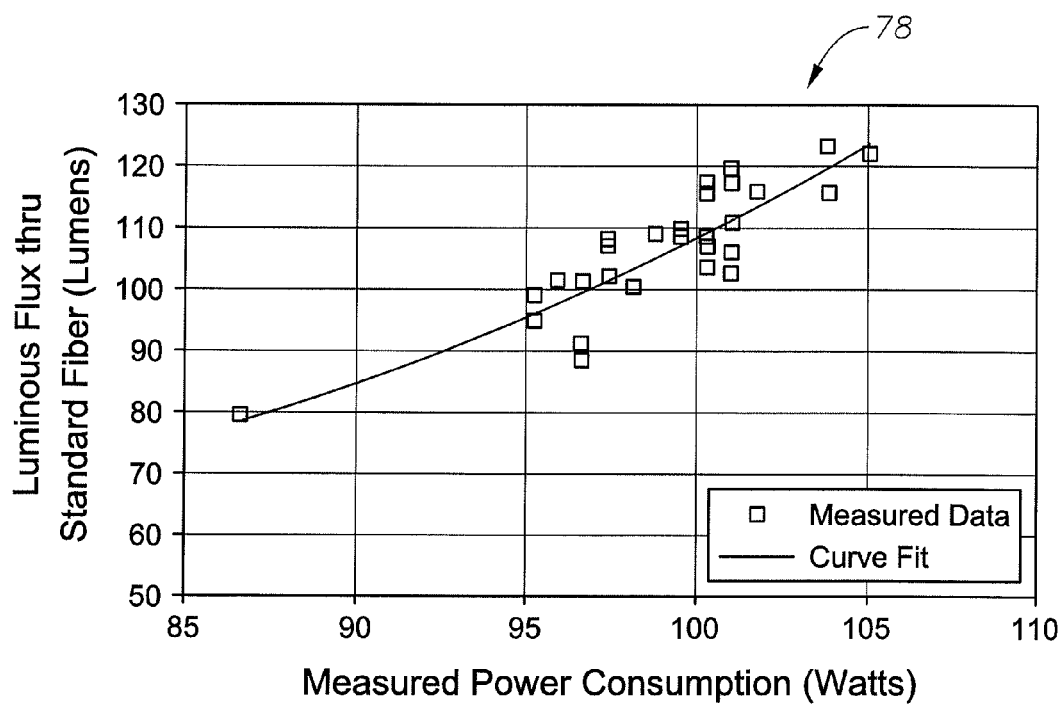
FIG. 4 illustrates an example of a lamp intensity function according to certain embodiments.

FIG. 4 illustrates an example of a lamp intensity function. Diagram 78 shows an example of a lamp intensity function determined from data describing measured power consumption (given in watts) and luminous flux (given in lumens). A function may be calculated from data using any suitable curve-fitting technique.

Figure 5:
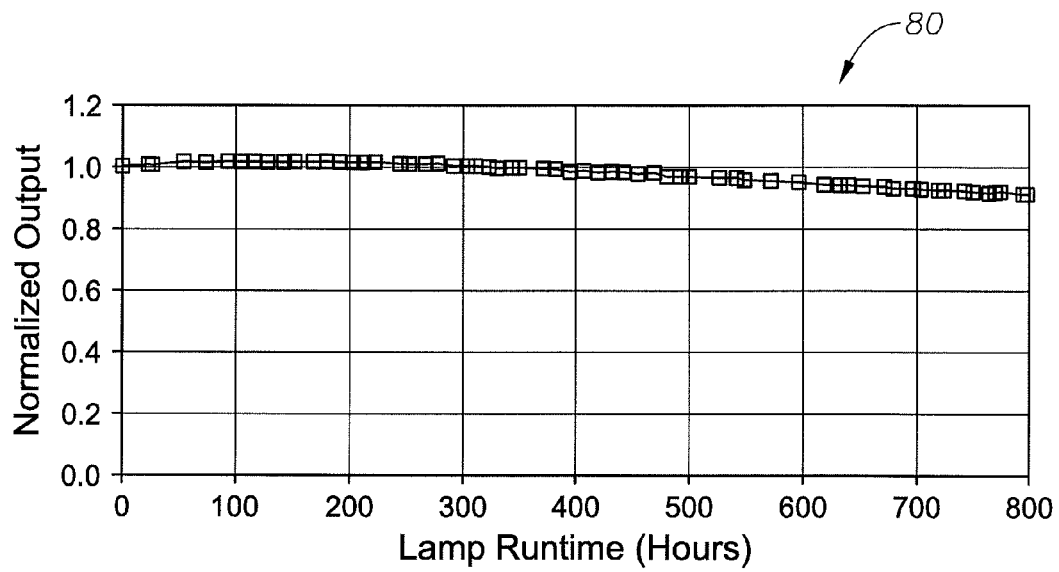
FIG. 5 illustrates an example of a lamp intensity degradation function according to certain embodiments.

FIG. 5 illustrates an example of a lamp intensity degradation function. Diagram 78 shows an example of a lamp output with respect to lamp age (given in hours). The lamp output is normalized with respect to the maximum output of the lamp.

Figure 6:
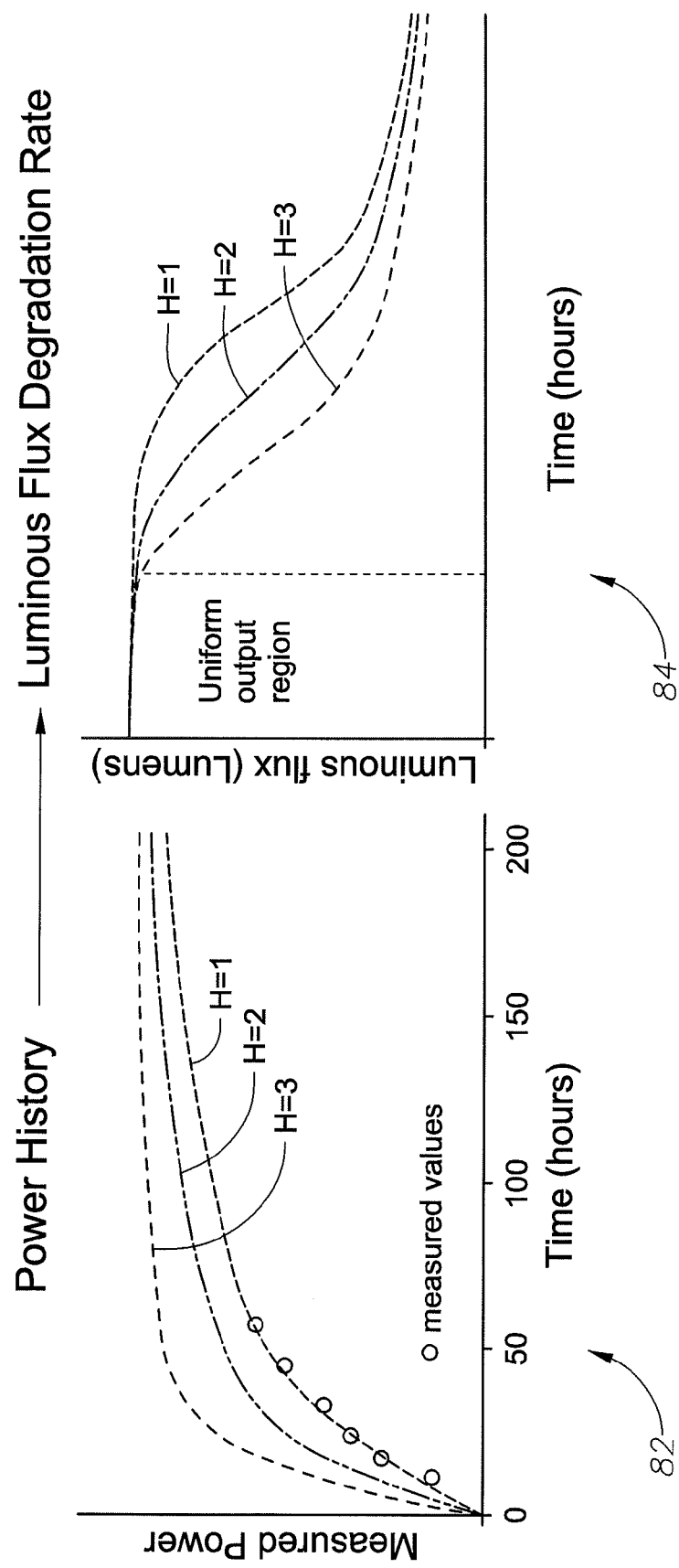
FIG. 6 illustrates an example of determining lamp performance using measured power.

FIG. 6 illustrates an example of determining lamp performance using measured power. Diagram 82 shows measured power with respect to lamp age for different lamps, where H is an index that represents the degradation rate characteristic of a particular type of lamp. Diagram 84 shows lamp performance with respect to lamp age for different lamps, which is determined from diagram 82.

For arc lamps, the rate of power increase is proportional to the physical size of the emitting spot on the arc lamp. The optical system reimages the emitting spot on the lamp to the entrance aperture of the fiber optic, so the coupling efficiency degrades inversely to the size of the lamp spot. Hence, for lamps that exhibit significant manufacturing variation, monitoring the rate of power consumption increase over lamp burn life enables the system to select the appropriate lamp performance degradation factor curve (shown in 84). In certain embodiments, the index selection is made prior to when the lamp performance degradation factor curves diverge substantially (e.g., at 50 hours).

Figure 7:
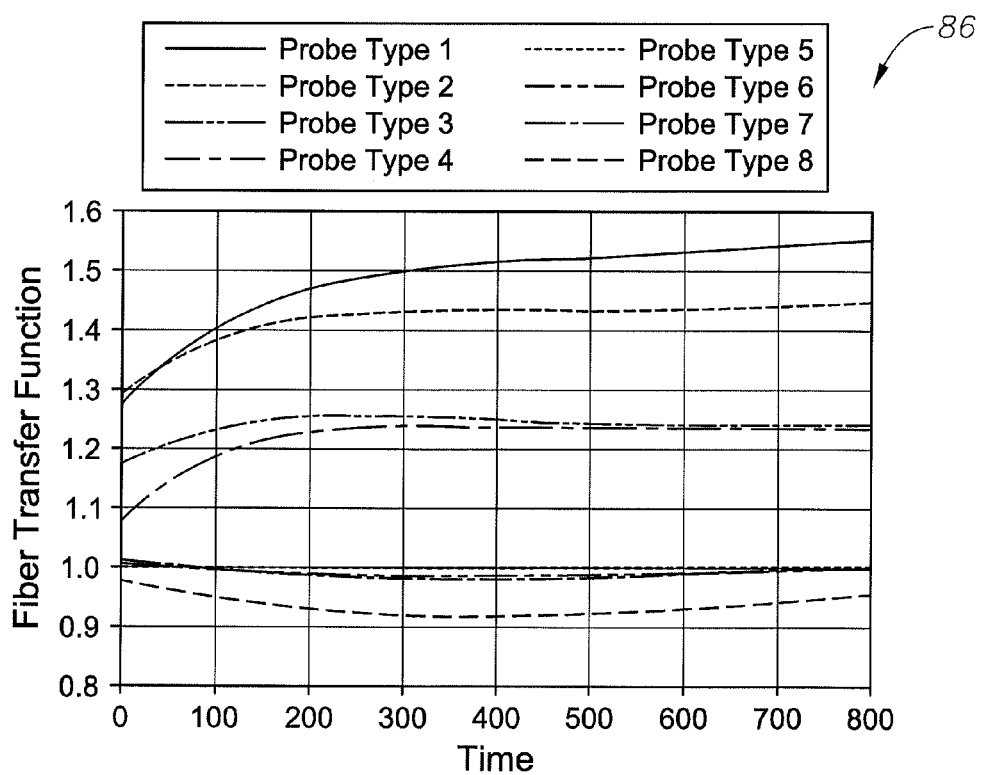
FIG. 7 illustrates examples of fiber transfer functions for different types of probes according to certain embodiments.

FIG. 7 illustrates examples of fiber transfer functions for different types of probes. Diagram 86 shows fiber transfer functions with respect to time (given in runtime hours of the lamp). A fiber transfer function (FTF) may be expressed as the ratio of luminous flux for the probe to that of a glass fiber standard (GFS), divided by the probe UFR, that is, FTF=luminous flux from probe/(luminous flux from GFS *UFR of probe).

A component of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A method for determining an endoilluminator output comprising:
   establishing a lamp performance degradation factor of a lamp of an endoilluminator system;
   calculating an illuminator contribution of the lamp using the lamp performance degradation factor;
   calculating a fiber contribution of one or more optical fibers of the endoilluminator system; and
   determining the endoilluminator output of the endoilluminator system from the illuminator contribution and the fiber contribution.

2. The method of claim 1, further comprising:
   receiving a set point for the endoilluminator system; and
   adjusting one or more components of the endoilluminator system to match the endoilluminator output to the set point.

3. The method of claim 1, further comprising:
   monitoring lamp degradation of the lamp; and
   adjusting one or more components of the endoilluminator system to compensate for the lamp degradation.

4. The method of claim 1, the calculating the illuminator contribution further comprising:
   establishing an illuminator leg efficiency of the lamp; and
   calculating the illuminator contribution using the illuminator leg efficiency.

5. The method of claim 1, the calculating the illuminator contribution further comprising:
   establishing an attenuator factor of the lamp; and
   calculating the illuminator contribution using the attenuator factor.

6. The method of claim 1, the calculating the illuminator contribution further comprising:
   establishing an initial lamp performance of the lamp; and
   calculating the illuminator contribution using the initial lamp performance.

7. The method of claim 1, the calculating the fiber contribution further comprising:
   establishing a fiber coupling factor of the one or more fibers; and
   calculating the fiber contribution using the fiber coupling factor.

8. The method of claim 1, the calculating the fiber contribution further comprising:
   establishing a fiber transmission ratio of the one or more fibers; and
   calculating the fiber contribution using the fiber transmission ratio.

9. The method of claim 1, further comprising:
   determining a next initial lamp performance of a next lamp;
   calculating a next illuminator contribution of the next lamp using the next initial lamp performance; and
   determining a next endoilluminator output of the endoilluminator system from the next illuminator contribution and the fiber contribution.

10. The method of claim 1, further comprising:
    collecting information to determine the endoilluminator output using wireless or wired communication, a stored lookup table, user input, or a monitoring device.

11. A system for determining an endoilluminator output comprising:
    one or more memories configured to store a lamp performance degradation factor of a lamp of an endoilluminator system; and
    one or more processors configured to:
      calculate an illuminator contribution of the lamp using the lamp performance degradation factor;
      calculate a fiber contribution of one or more optical fibers of the endoilluminator system; and
      determine the endoilluminator output of the endoilluminator system from the illuminator contribution and the fiber contribution.

12. The system of claim 11, the one or more processors further configured to:
    receive a set point for the endoilluminator system; and
    adjust one or more components of the endoilluminator system to match the endoilluminator output to the set point.

13. The system of claim 11, the one or more processors further configured to:
    monitor lamp degradation of the lamp; and
    adjust one or more components of the endoilluminator system to compensate for the lamp degradation.

14. The system of claim 11, the calculating the illuminator contribution further comprising:
    establishing an illuminator leg efficiency of the lamp; and
    calculating the illuminator contribution using the illuminator leg efficiency.

15. The system of claim 11, the calculating the illuminator contribution further comprising:
    establishing an attenuator factor of the lamp; and
    calculating the illuminator contribution using the attenuator factor.

16. The system of claim 11, the calculating the illuminator contribution further comprising:
    establishing an initial lamp performance of the lamp; and
    calculating the illuminator contribution using the initial lamp performance.

17. The system of claim 11, the calculating the fiber contribution further comprising:
    establishing a fiber coupling factor of the one or more fibers; and
    calculating the fiber contribution using the fiber coupling factor.

18. The system of claim 11, the calculating the fiber contribution further comprising:
    establishing a fiber transmission ratio of the one or more fibers; and
    calculating the fiber contribution using the fiber transmission ratio.

19. The system of claim 11, the one or more processors further configured to:
    determine a next initial lamp performance of a next lamp;
    calculate a next illuminator contribution of the next lamp using the next initial lamp performance; and
    determine a next endoilluminator output of the endoilluminator system from the next illuminator contribution and the fiber contribution.

20. The system of claim 11, the one or more processors further configured to:
    collect information to determine the endoilluminator output using wireless or wired communication, a stored lookup table, user input, or a monitoring device.

21. A method for determining an endoilluminator output comprising:
    establishing an initial lamp performance;
    calculating an illuminator contribution using the initial lamp performance;

calculating a fiber contribution; and determining the endoilluminator output from the illuminator contribution and the fiber contribution.

22. The method of claim 21, further comprising:

receiving a set point for the endoilluminator system; and adjusting one or more components of the endoilluminator system to match the endoilluminator output to the set point.

23. The method of claim 21, further comprising:

monitoring lamp degradation of the lamp; and adjusting one or more components of the endoilluminator system to compensate for the lamp degradation.

24. A method for determining an endoilluminator output comprising:

establishing a fiber coupling factor;

calculating a fiber contribution using the fiber coupling factor;

calculating an illuminator contribution; and determining the endoilluminator output from the fiber contribution and the illuminator contribution.

25. The method of claim 24, further comprising:

receiving a set point for the endoilluminator system; and adjusting one or more components of the endoilluminator system to match the endoilluminator output to the set point.

26. The method of claim 24, further comprising:

monitoring lamp degradation of the lamp; and adjusting one or more components of the endoilluminator system to compensate for the lamp degradation.

\* \* \* \* \*